United States Patent
Hutchins et al.

(10) Patent No.: US 10,297,347 B2
(45) Date of Patent: May 21, 2019

(54) ADVERSE EVENT PRIORITIZATION AND HANDLING

(71) Applicant: PREVENTICE, INC., Rochester, MN (US)

(72) Inventors: James D. Hutchins, Kernersville, NC (US); Richard M. Smith, Oronoco, MN (US)

(73) Assignee: Preventice Solutions, Inc., Rochester, MN (US)

( * ) Notice: Subject to any disclaimer, the term of this patent is extended or adjusted under 35 U.S.C. 154(b) by 1011 days.

(21) Appl. No.: 14/679,793

(22) Filed: Apr. 6, 2015

(65) Prior Publication Data

US 2016/0292374 A1    Oct. 6, 2016

(51) Int. Cl.
| | | |
|---|---|---|
| *G16H 40/63* | (2018.01) | |
| *G06Q 10/06* | (2012.01) | |
| *H04L 29/08* | (2006.01) | |
| *G16H 40/20* | (2018.01) | |
| *G16H 50/30* | (2018.01) | |
| *G06F 19/00* | (2018.01) | |

(52) U.S. Cl.
CPC .......... *G16H 40/63* (2018.01); *G06F 19/00* (2013.01); *G06Q 10/0633* (2013.01); *G16H 40/20* (2018.01); *G16H 50/30* (2018.01); *H04L 67/12* (2013.01)

(58) Field of Classification Search
CPC ........ G06Q 50/22; G06Q 50/24; G06F 19/30; G06F 19/32; G06F 19/34; G06F 19/36; G16H 10/00; G16H 10/60; G16H 40/00; G16H 40/60
USPC ....................................... 705/2, 3
See application file for complete search history.

(56) References Cited

U.S. PATENT DOCUMENTS

| | | | | |
|---|---|---|---|---|
| 6,591,307 B1 * | 7/2003 | Arimilli | ............ | G06F 12/0813 709/201 |
| 6,823,512 B1 * | 11/2004 | Miller | ................ | H04L 1/1628 709/201 |
| 7,292,956 B1 * | 11/2007 | Guday | ................ | G16H 15/00 702/118 |

(Continued)

FOREIGN PATENT DOCUMENTS

WO     2012108940 A1    8/2012

OTHER PUBLICATIONS

International Search Report and Written Opinion for PCT/US2016/026020, dated Jul. 6, 2016.

*Primary Examiner* — Jason S Tiedeman
(74) *Attorney, Agent, or Firm* — Patterson + Sheridan, LLP

(57) ABSTRACT

Collecting biometric data from a patient provides numerous opportunities for a care provider to monitor the health of the patient. In one embodiment, the biometric data is used to identify health events that are processed in a workflow that includes a plurality of interconnected processing nodes and queues. In one embodiment, the workflow processes the health events using a priority assigned to the health events. The priority may be assigned based on a severity of the event, the type of the health event, a characteristic of the patient whose biometric data generated the health event, and the like. Each processing node in the event engine may include multiple consumers or threads for processing health events with different priorities. By having more consumers assigned to high priority events, the latency for processing these events in the workflow may be reduced.

20 Claims, 6 Drawing Sheets

(56) References Cited

U.S. PATENT DOCUMENTS

| | | | | |
|---|---|---|---|---|
| 8,549,530 B1* | 10/2013 | Bullock | G06F 9/5083 | 718/102 |
| 2002/0013517 A1* | 1/2002 | West | G16H 40/20 | 600/300 |
| 2002/0128871 A1* | 9/2002 | Adamson | G06Q 10/10 | 705/3 |
| 2004/0148193 A1* | 7/2004 | Blackburn | A61B 5/0002 | 705/2 |
| 2005/0144234 A1* | 6/2005 | Tanaka | G06F 9/4881 | 709/205 |
| 2006/0053035 A1* | 3/2006 | Eisenberg | G06Q 50/22 | 705/2 |
| 2007/0013511 A1* | 1/2007 | Weiner | A61B 5/0002 | 340/539.12 |
| 2009/0182576 A1* | 7/2009 | Warner | G06F 19/327 | 705/2 |
| 2010/0305966 A1* | 12/2010 | Coulter | G06Q 10/04 | 705/2 |
| 2011/0078411 A1* | 3/2011 | Maclinovsky | G06Q 10/06 | 712/30 |
| 2012/0190955 A1* | 7/2012 | Rao | A61M 5/142 | 600/368 |
| 2012/0245435 A1* | 9/2012 | Corpier | A61B 5/746 | 600/300 |
| 2013/0097272 A1* | 4/2013 | Atkins | G06F 11/0709 | 709/207 |
| 2013/0152097 A1* | 6/2013 | Boctor | G06F 9/505 | 718/103 |
| 2013/0179897 A1* | 7/2013 | Archer | G06F 9/4893 | 718/108 |
| 2013/0197942 A1* | 8/2013 | Chiu | G06Q 50/22 | 705/3 |
| 2013/0247066 A1* | 9/2013 | Dodge | G06F 9/4881 | 718/104 |
| 2014/0156291 A1* | 6/2014 | Kozicki | G06Q 30/0631 | 705/2 |
| 2014/0249848 A1* | 9/2014 | Averill | G06Q 50/24 | 705/3 |
| 2014/0331322 A1* | 11/2014 | Jaroch | H04L 63/1416 | 726/23 |
| 2015/0212794 A1* | 7/2015 | Otenko | G06F 9/52 | 710/109 |
| 2017/0109492 A1* | 4/2017 | McCullough | G16H 50/30 | |

* cited by examiner

ADVERSE EVENT PRIORITIZATION AND HANDLING

BACKGROUND

Field

Embodiments presented herein generally describe software tools to health care, and more specifically, for processing prioritized health events in a workflow.

Description of the Related Art

The Internet of Things (IoT) generally refers to the ability of many devices, aside from conventional computing platforms, to connect to computer networks. In the health care field, the ability to network virtually any devices allows a person's health to be monitored outside of a hospital or physician office. For example, network aware devices may be embedded in clothing, worn using a support device, or located in user's house. Sensors in such devices can communicate with a mobile device carried by the user (e.g., a mobile phone or tablet) or a remote system over a network. The mobile device can forward data received from the sensors to remote computing systems for processing as well as perform processing locally.

Using the data retrieved from the sensors, a physician can monitor the health of the patient remotely. For example, a physician can check in on a patient to monitor her heart rate, blood pressure, or check for changes in weight using the data collected by the sensors. The physician can then determine whether a change to the patient's treatment is needed—e.g., changing medication dosage, scheduling an additional physician visit, and the like.

SUMMARY

One embodiment provides a method for processing health events in a workflow. The method includes receiving a health event for a patient derived from monitoring biometric data generated by one or more sensor devices and identifying a type of the health event by classifying biometric data associated with the health event. The method includes processing the health event using a plurality of interconnected processing nodes based on the type of the health event and a priority assigned to the health event, where each processing node comprises respective sets of consumers and each set is assigned to process health events at a different priority level.

Additional embodiments provide a computer-readable medium and system for carrying out the aforementioned method.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
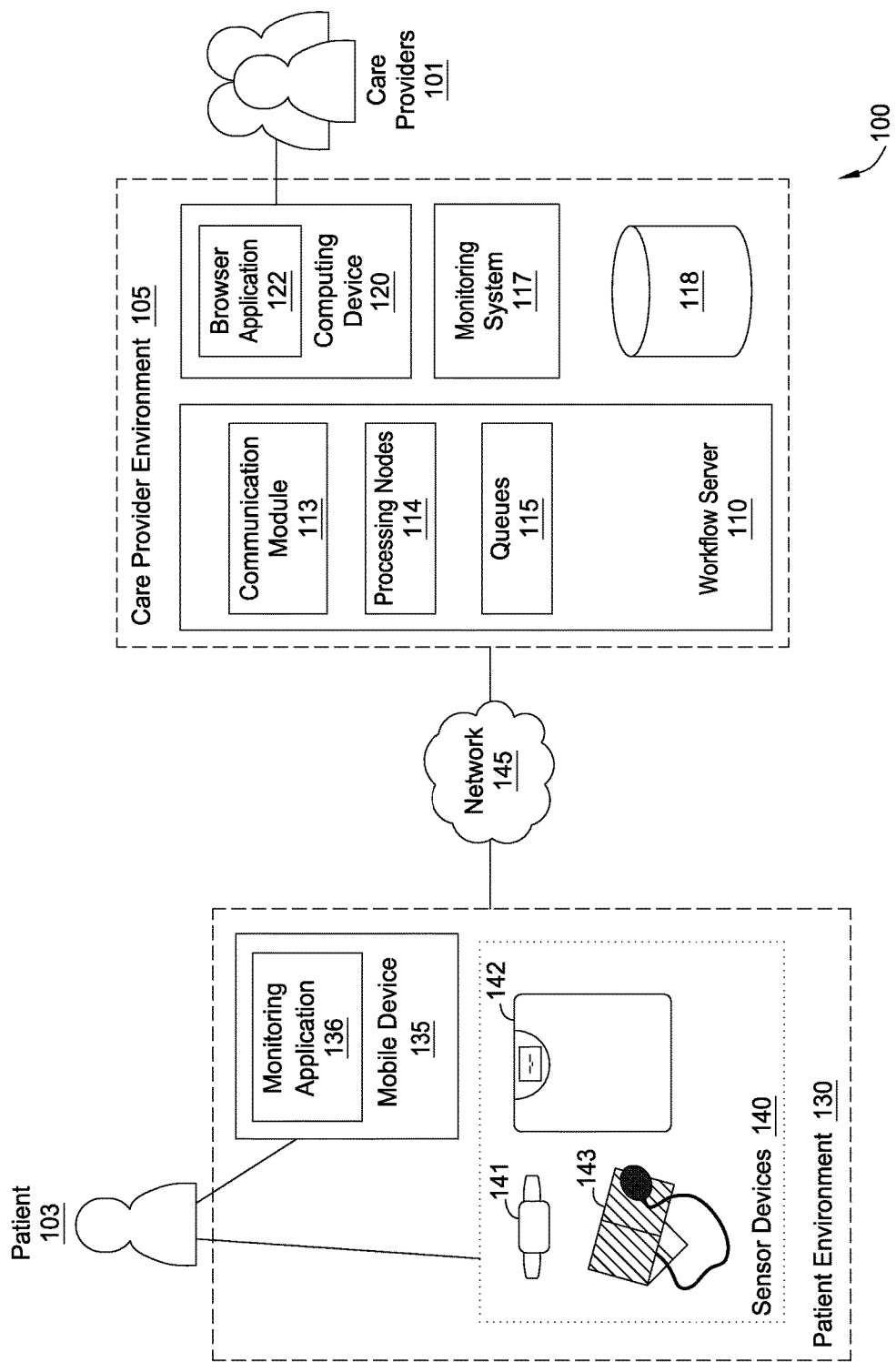
FIG. 1 illustrates an example computing environment, according to one embodiment.

Network aware devices provide a variety of opportunities for a care provider (e.g., a physician, nurse, technician, etc.) to improve patient care. An event manager can use the data provided by network aware devices or an "internet of things" (IoT) device to identify health events that range from identifying critical health care issues such as cardiac or respiratory emergencies to maintenance events where the network aware device fails, e.g., because a battery is low or a wire is disconnected. To process health related events, an event manager may process events using a collection of defined paths.

In one embodiment, a group of servers each host an event engine with a respective set of interconnected tasks and queues that form a workflow. The group of servers may include a load balancer which routes the biometric measured by the IoT devices to one of the servers for processing. Because the data is processed using different tasks, the event engines can process multiple health events simultaneously. Stated differently, the event engines process the health events using a series of steps in the workflow where each step (or task) can process a respective health event in parallel.

In one embodiment, the event engines classify health events received from the body worn sensor devices. For example, a device may have classified the health event as one type of event. However, the workflows in the event engines may process the biometric data associated with the event to confirm the initial classification or reclassify or reprioritize the health event as a different type of event. Alternatively, the sensor device may send biometric data to the servers which then use one or more thresholds or rules to identify health events which are then processed by the workflows in the event engines. The workflows determine actions to take when processing the health events such as notifying a care provider, suppressing or ignoring the event, or storing the event in a data repository.

In one embodiment, the workflows process the health events using a priority assigned to the health events. The priority may be assigned based on a severity of the event (e.g., an irregular heart beat versus a heart attack), the type of the health event, a characteristic of the patient whose biometric data generated the health event (e.g., the patient's age or past medical history), and the like. Processing nodes in the workflows may include multiple consumers (e.g., processing threads) for processing different priority health events. For example, a processing node may include ten consumers assigned to process high priority events, seven consumers assigned to process medium priority events, and five consumers assigned to process low priority events. By having more consumers assigned to high priority events, the latency for processing these events in the workflow may be reduced. In another example, the consumers assigned to process the higher priority health events may have more computer resources assigned to them—e.g., additional CPUs or memory—than consumers that process lower priority events in the node.

FIG. 1 illustrates an example computing environment 100, according to one embodiment. As shown, the computing environment 100 may include a care provider environment 105 and a patient environment 130, each connected to one another via a network 145. The environments 105 and 130 allow a care provider 101 (e.g., a technician, nurse, physician, etc.) to monitor biometric data generated by the patient 103.

The care provider environment 105 includes workflow server 110, a computing device 120, monitoring system 117 and data repository 118. Each of the workflow server 110, device 120, and monitoring system 125 may be a physical computing system that includes one or more computing devices or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

The workflow server 110 includes applications and data executed to identify and handle health events corresponding to patients 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and queues 115 which form a workflow. As biometric data or health events are received from the patient environment 130, the workflow may classify (or reclassify) the data to identify a type of the health event— e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated an electrode has become detached triggers a maintenance event. In one embodiment, the sensor devices 140 or monitoring application 136 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more processing nodes 114 or queues 115 and be immediately displayed to a care provider 101 using the monitoring system 117.

The communication module 113 permits the workflow server 110 to receive data from the patient environment 130 and transmit data to the care providers 101. The communication module 113 may receive data from the sensor devices 140 which is used to identify a health event and a corresponding path through the interconnected processing nodes 114 and queues 115. The communication module 113 can use monitoring system 117 and computing device 120 to help the care providers 101 complete the workflow. Moreover, in addition to receiving information from the patient environment 130, the communication module 113 may enable the workflow server 110 to transmit requests or instructions to the patient environment 130 such as asking the patient 103 if she has any symptoms or instructing the patient 103 to reattach a disconnected electrode.

In one embodiment, the path used by a health event to traverse the workflow server 110 may include processing nodes 114 that process health events without user intervention as well as processing nodes 114 that require input from the care providers 101. For example, a processing node 114 may filter or screen a health event to determine what queue to place the event, compare the event to one or more rules to determine an action to perform, or store the event. Alternatively, some processing nodes 114 may require the care provider 101 to perform an action or provide instructions. For example, the monitoring system 117 may generate a UI for a health event which is then displayed to the care provider 101 by the browser application 122. Once the care provider 101 performs an action (e.g., confirms the classification of the event or agrees with an action suggested by the workflow server 110), the remaining steps of the workflow are performed—e.g., send a notification to the patient 103, log the event in the history of the patient 103, route the event to a different care provider 101, reclassify the event (if the care provider 101 indicated the initial classification was incorrect), or prioritize or triage the event.

As shown, patient environment 130 includes a mobile device 135 and sensor devices 140. The mobile device 135 includes a monitoring application 136 which permits communication between the sensor devices 140 and the care provider environment 105 via network 145. The monitoring application 136 may configure one or more sensor devices 140 (e.g., IoT devices) to monitor one or more patients' biometric data as specified by a care plan. For example, the application 136 could configure logic on a heart rate monitor device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitor device, upon detecting that a threshold condition has been satisfied, could generate and transmit a health event to the mobile device 135, which in turn transmits the event to the workflow server 110 for processing. However, in other embodiments, some of the tasks performed by the workflow server 110 may be performed by the mobile device 135. That is, the workflow may include tasks performed by the mobile device 135 or sensor device 140 as well as tasks performed by the workflow server 110.

In one embodiment, the monitoring application 136 receives environmental data from the sensor devices 140. Generally, the environmental data informs the monitoring application 136 of environmental conditions in an area proximate to the sensor device 140 and the user—e.g., a room in which the user is located. For example, the sensor devices 140 may detect the air quality or pollen count for a user who has a respiratory ailment. In another example, the sensor devices 140 may track the user's movements or actions in an environment such as how many times at night the user goes to the bathroom or if the user is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, a processing node 114 may ask the patient 103 if she is experiencing any symptoms. To get the patient's feedback, the monitoring application 136 may display a UI on the mobile device 135 which permits the patient 103 to list symptoms. Moreover, the application 136 may also display general information related to a care plan or the sensor devices 140 such as the patient's heart rate or weight, status of the sensors devices 140, etc.

In one embodiment, sensor devices 140 interact with monitoring application 136 and assist the patient 103 in reporting patient vitals and other information to the care provider environment 105. As shown, such sensor devices 140 may include a body sensor 141, a weighing scale 142, and a blood pressure cuff 143. Each of the sensor devices 140 may capture different vitals of the patient 103. For example, when applied to the body of patient 103, the body sensor 141 captures biometric data (e.g., heart rate, ECG data, etc.) in real-time. In addition, each of the sensor devices 140 may be configured to transmit the body-related metrics electronically to the monitoring application 136 on the mobile device 135. In turn, the monitoring application 136 sends the captured metrics to the workflow server 110 which can be used to trigger health events which are processed using the processing nodes 114 and queues 115.

In one embodiment, upon detecting an observation threshold has been reached, the sensor devices 140 perform an initial classification of the health event. In a particular embodiment, the mobile device 135 is configured to perform the initial classification of the health event. For example, the body sensor 141, upon detecting that the ECG data collected from the patient 103 indicates an erratic heart behavior, could classify the health event as a cardiac event. This initial classification, along with the relevant ECG data (e.g., ECG data a predetermined length of time before and after the event), could be transmitted to the mobile device 135 (e.g., over a Bluetooth® communications link) where the monitoring application 136 forwards the health event data on to the workflow server 110 over the network 145 (e.g., the Internet). Alternatively, instead of classifying the data, the monitoring application 136 may forward the raw, unprocessed sensor data to the event manager 110 which uses one of the processing nodes 114 to identify and classify health events which are then processed in the workflow server 110.

Figure 2:
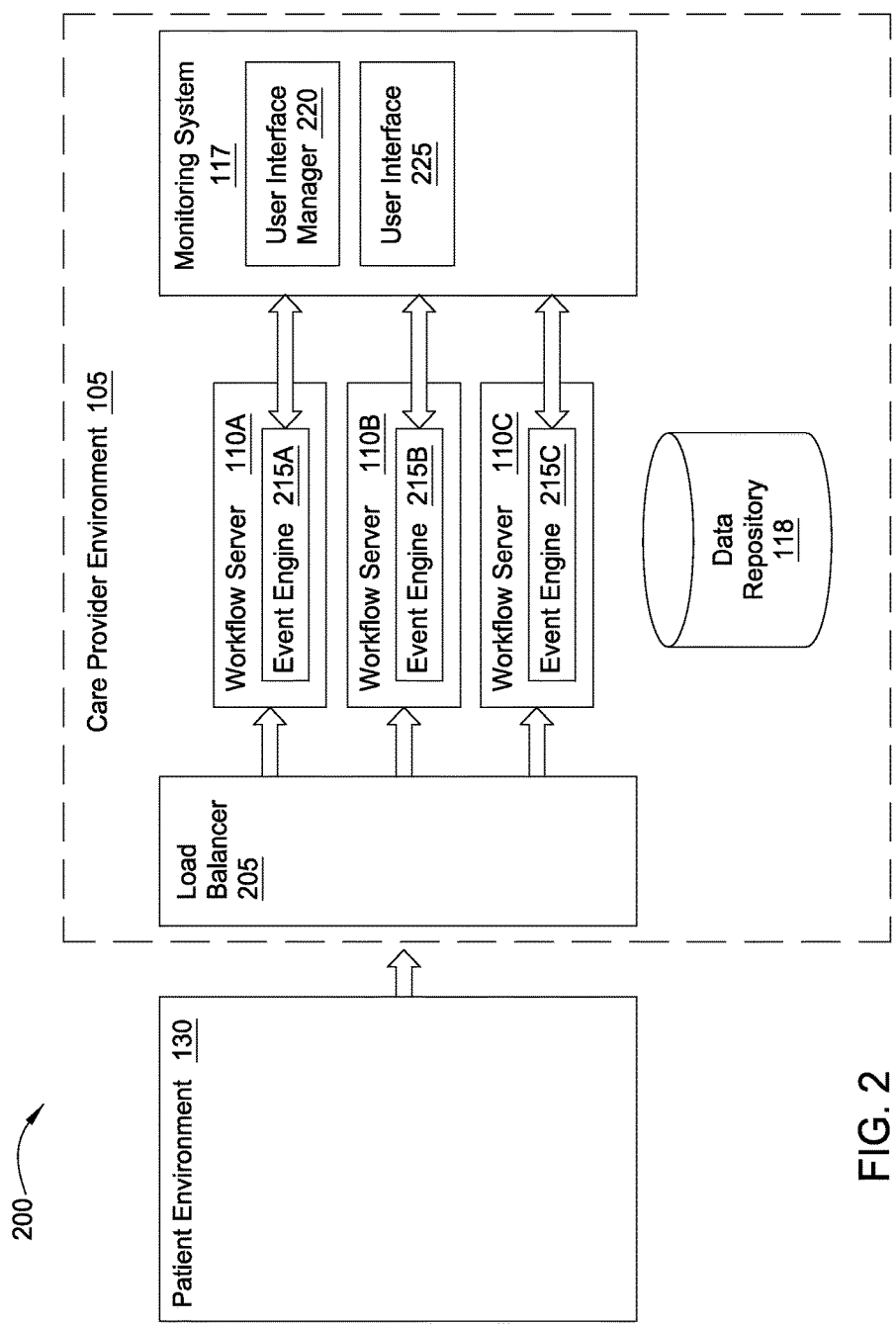
FIG. 2 illustrates a parallel processing computing environment, according to one embodiment.

FIG. 2 illustrates a parallel processing computing environment 200, according to one embodiment. As shown, the patient environment 130 transmits biometric data or health events to the care provider environment 105 which includes a load balancer 205. The workflow servers 110 each include an event engine 215. Although not shown, each event engine 215 includes a plurality of interconnected processing nodes and queues that form a workflow for processing health events as discussed above. In one embodiment, the event engines 215 each includes the same processing nodes and queues arranged in the same manner such that any one of the event engines 215 can process the different health events generated by the sensor devices—i.e., any one of the event engines 215 can process a cardiac event, respiratory event, maintenance event, etc. Based on current workload, the load balancer 205 transmits received data or heath events to one of the servers 110 for processing. For example, the load balancer 205 may assign the received health events in a round robin manner or by monitoring the CPU or memory usage of the servers 110.

Alternatively, the event engines 215 may have different processing nodes and queues (or a different arrangement of the nodes and queues) such that the event engines 215 are configured to process different event types. For example, event engines 215A and 215B may have workflows that process cardiac events (and have the same processing nodes and queues), while the workflow in event engine 215C processes respiratory events. The load balancer 205 may determine which event engine 215 should receive the health event using the initial classification provided by the patient environment 130 or based on which sensor device measured the biometric data.

Regardless whether the event engines have the same arrangement or different arrangements, compute resources can easily be adjusted in response to varying workloads. For example, as more sensor devices are added to the patient environment 130, a system administrator can add additional workflow servers 110 to process the increased number of received health events. The reverse is also true. If the number of health events decreases, the administrator may remove one or more of the workflow servers 110. For example, if event engine 215A and 215B both process cardiac events but the number of cardiac events has decreased, the system administrator may remove one of the servers 110A or 110B.

Monitoring system 117 includes a UI manager 220 and UI 225. As discussed above, the processing nodes may require input from a care provider in order to route the health events through the event engines 215. To do so, the event engines 215 transmit requests to the UI manager 220 which generates a UI 225 which can be displayed to a care provider. For example, the UI manager may generate a UI 225 that includes an electrocardiogram (ECG) chart corresponding to a cardiac event. Further, the UI 225 may include I/O features (e.g., buttons or pull down menus) that the care provider can use to provide input or instructions to the event engine 215. For example, the care provider may instruct the event engine 215 to store the cardiac event in the data repository 118, send the cardiac event to a queue that is monitored by another care provider (e.g., to get a second opinion), or forward the cardiac event to the patient's primary physician. Thus, the monitoring system 117 permits the workflow servers 110 to output information to a care provider as well as receive instructions from the care providers.

The event engines 215 may store data in and retrieve data from the data repository 118. For example, the event engines 215 may maintain a patient history by storing all the received health events (or selected health events) derived based on monitoring a patient's vitals in the repository 118. Further, the event engines 215 may use the data stored in the data repository 118 to process the health events. For example, if the event engine 215 receives biometric data indicating the current weight of a patient, the engine 215 can retrieve past weight measurements for the patient from the data repository 118 and derive a trend graph detailing how the patient's weight has changed over time. For instance, the patient's current weight may not be enough to trigger a health event, but the patient's derived weight change over a period of time may trigger a health event. As discussed below, these derived trends may be used to generate a derived observation.

In one embodiment, the event engines 215 prioritizes health events, which, in turn, determines how quickly the health events are processed by the workflows in the engines 215 or what processing nodes and queues are used to process the health events. As discussed above, the health events may be prioritized based on a severity of the event, the type of the health event, a characteristic of the patient whose biometric data generated the health event, and the like.

Figure 3:
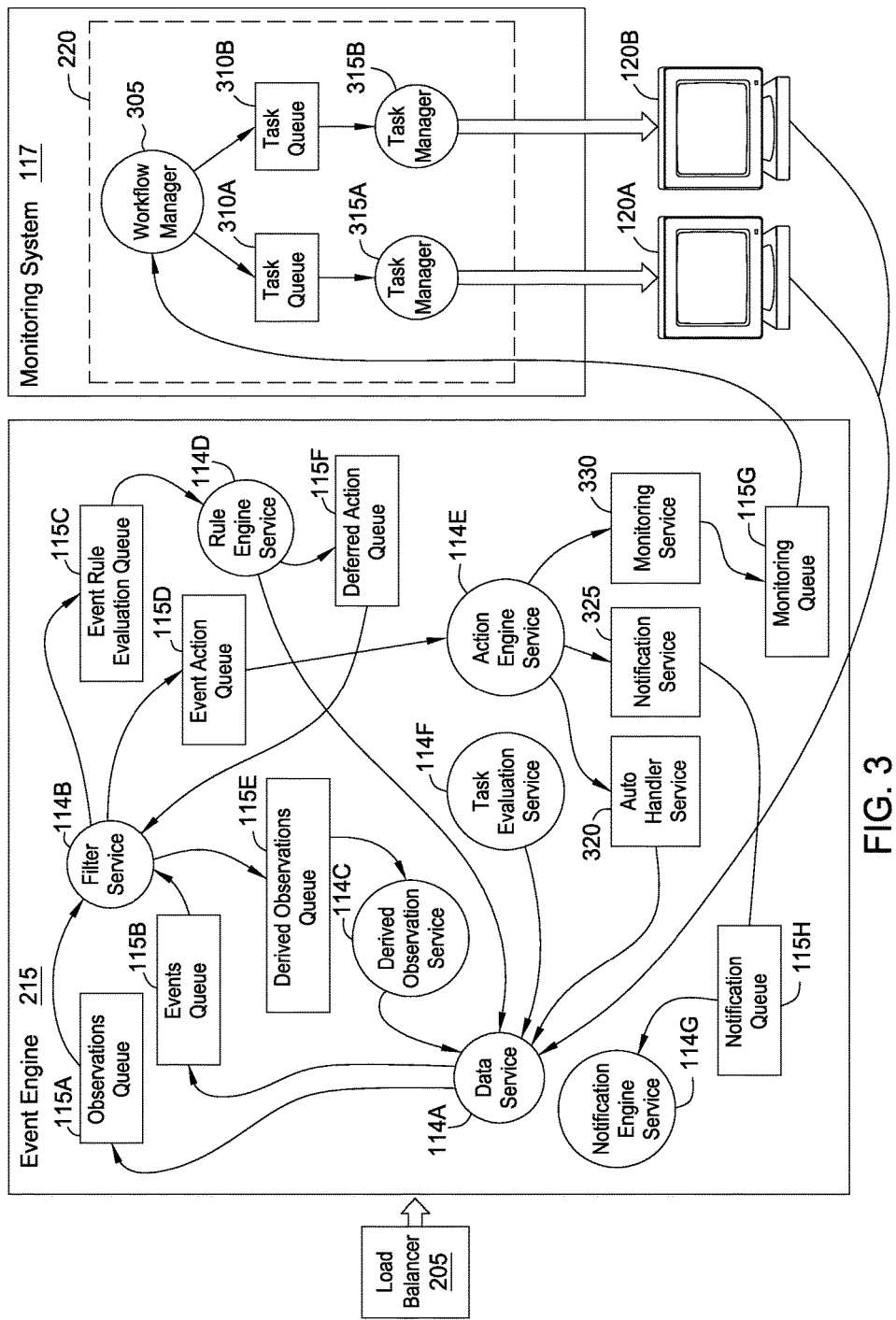
FIG. 3 illustrates an event engine for processing received health events, according to one embodiment.

FIG. 3 illustrates an event engine 215 that includes a workflow for processing health events, according to one embodiment. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 114B. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 114B and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 315, notification service 320, or monitoring service 325. The auto handler service 315 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, care provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear a sensor device for certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Figure 4:
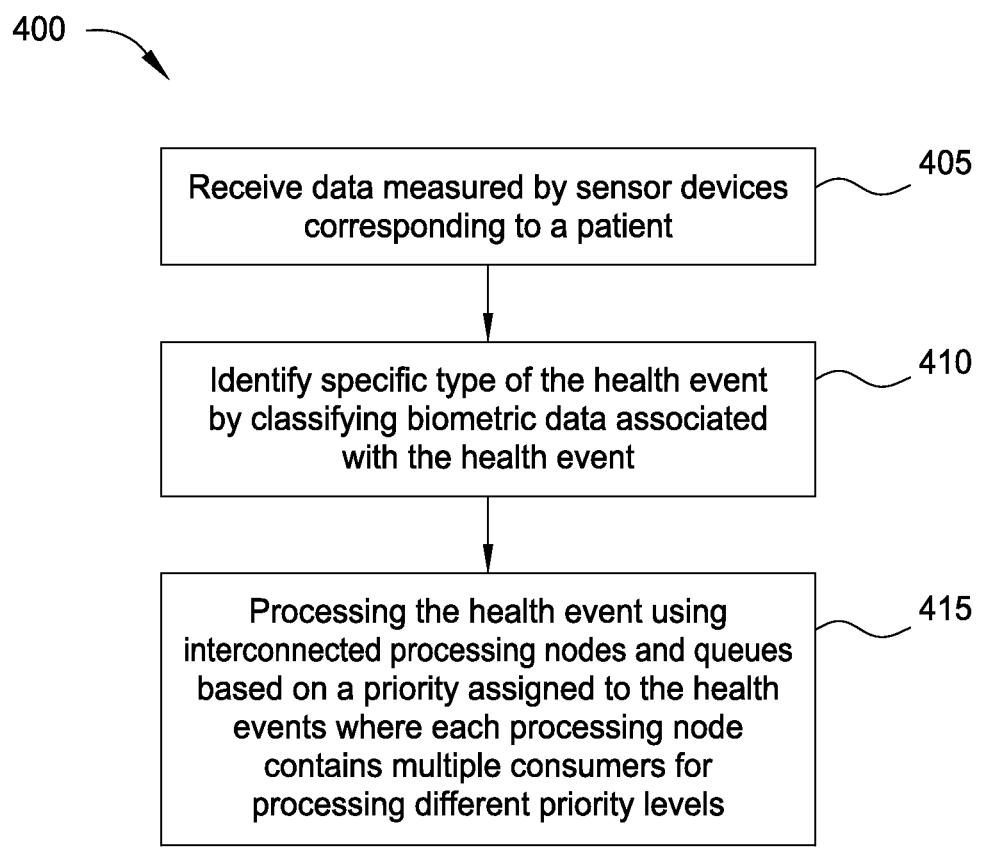
FIG. 4 is a flowchart for processing health events in a workflow, according to one embodiment.

FIG. 4 is a flowchart 400 for processing health events in a workflow, according to one embodiment. At block 405, the workflow receives data measured by sensor devices corresponding to a patient. This data may be observations (e.g., measured weight changes, blood pressure changes, ECG data, or blood oxygen levels) or health events (e.g., biometric data or maintenance data that satisfy one or more conditions). As discussed above, the observations may be raw data measured by the sensor devices, while the health events are generated by the sensor devices or a patient's computing device processing the raw sensor data to see if, for example, the patient has an irregular heart beat or blood pressure that is above a threshold.

At step 410, the workflow classifies the received data to determine a type of the health event. For example, the workflow may determine that the health event is certain type of event such as cardiac, respiratory or maintenance event. The workflow may also distinguish between different subtypes of events such as determining whether an irregular heart beat (e.g., a cardiac event) is a ventricular trigeminy event or an atrioventricular block event.

At step 415, the workflow processes the health events (and observations) using a plurality of interconnected processing nodes and queues. In one embodiment, the workflow may be executed by one of the event engines 215 shown in FIGS. 2 and 3. In addition to the functionality discussed above, nodes may process health events based on an assigned priority.

Figure 5:
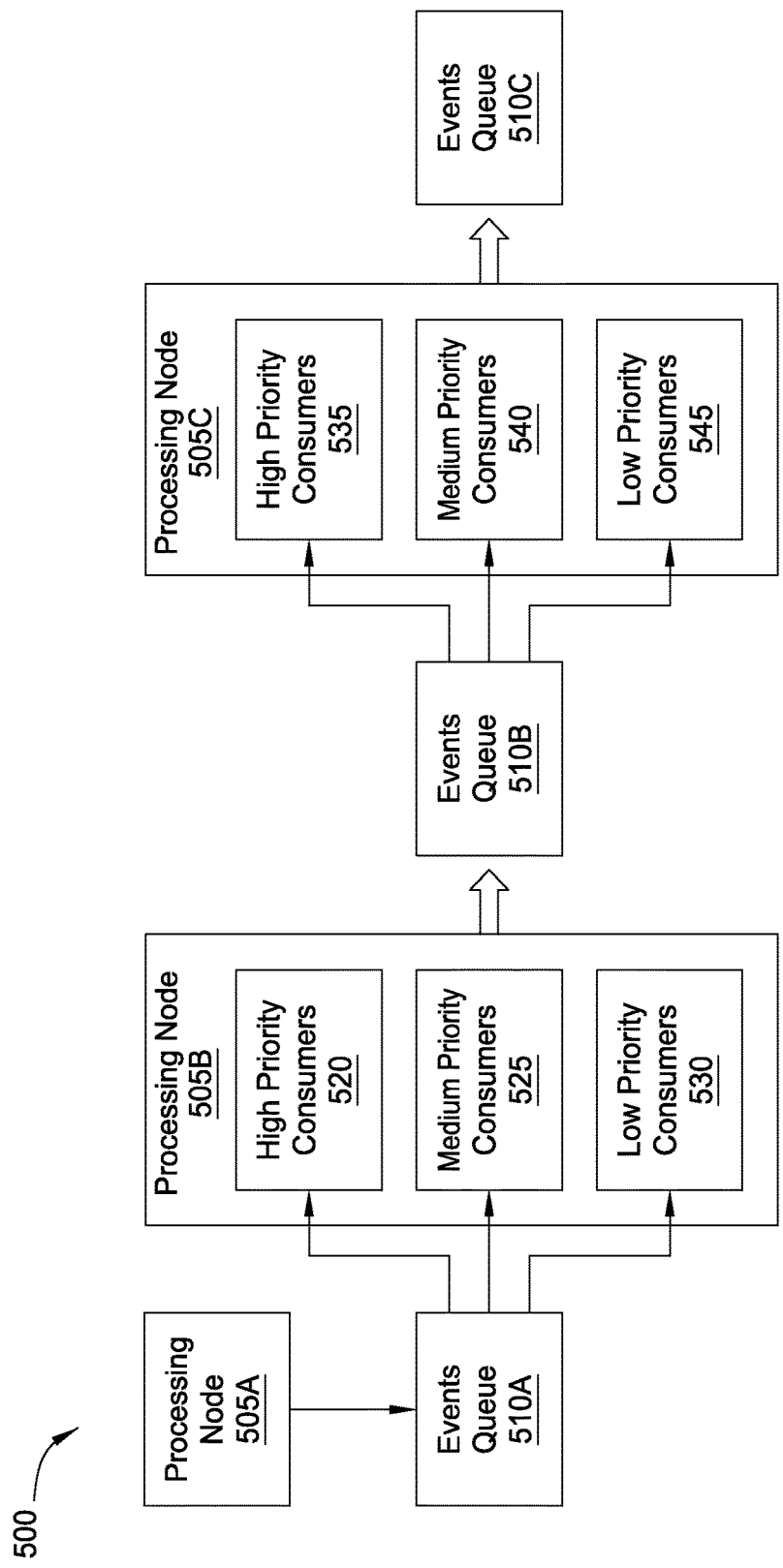
FIG. 5 illustrates a workflow with prioritized health events, according to one embodiment.

FIG. 5 illustrates a workflow 500 with prioritized health events, according to one embodiment. As shown, the workflow 500 includes processing nodes 505 coupled to queues 510. Like the processing nodes 114 in FIG. 3, the processing nodes 505 may perform a variety of tasks or actions as part of a workflow. In addition, processing nodes 505B and 505C contain different sets of consumers assigned to process health events with different priorities. That is, node 505B includes high priority consumers 520 for processing high priority health events, medium priority consumers 525 for processing medium priority health events, and low priority consumers 530 for processing low priority health events. While the consumers in processing node 505B may be assigned to different priority health events, the consumers may process the health events in the same manner. Stated differently, the consumers may contain the same logic for processing the health events, regardless of whether the health event is processed by the high priority consumers 520 or the low priority consumers 530, the result is the same. Thus, each consumer in processing node 505B may contain the same logic for processing the health events, while each consumer in processing node 505C also contains the same logic for processing the health events. In one embodiment, the consumers in the same processing node 505 may be different instances of the same thread (or process). In one embodiment, the higher priority events may be processed differently than the lower priority events. Put differently, high priority consumers 520 may process the high priority events different than how medium priority consumers 525 process medium priority events. For example, high priority consumers 520 may evaluate the triage corresponding to the event, assign the priority level to the event, and re-queue the event without performing more in depth (but slower) calculations like that performed by the medium priority consumers 525. In this example, the high priority events may move quicker through certain processing nodes 505 than the lower priority events. Nonetheless, the consumers 520, 525, and 530 may have one or more thread in common even if the overall process performed by the consumers is different.

While consumers in processing node 505 process the health events in the same manner, the processing nodes 505 may have different numbers of the consumers assigned to each priority level. For example, processing node 505B may have greater number of high priority consumers 520 than medium priority consumers 525 and low priority consumers 530. By having a greater number of high priority consumers 520 monitoring the upstream queues (e.g., queue 510A), the workflow 500 reduces the latency time that a high priority health event will likely wait in the upstream queue before being retrieved and processed by a high priority consumer. For example, processing node 505B may include ten high priority consumers 520, seven medium priority consumers 525, and five low priority consumers 530 which can each process a health event in parallel. Because node 505B includes more high priority consumers 520 (assuming the same number of high, medium, and low priority health events are received at the queue 510A), the high priority health events will have shorter wait times in the queue 510A than the other priority health events.

In one embodiment, the workflow 500 may use fast or additional computing resource for executing the high priority consumers than the medium or low priority consumers. That is, even if the numbers of high, medium, and low consumers are the same, the processing nodes 505 may nonetheless provide the high priority health events with reduced wait times by, for example, executing the high priority consumers using faster CPUs, or permitting the high priority consumers to access to greater amounts of memory than the medium or low priority consumers.

Advantageously, by assigning a different number of consumers to different priority levels, the workflow 500 can be easily changed in response to varying workloads. For example, if the rate at which high priority health events are received in queue 510A increases, a system administrator or a workflow manager (e.g., a software application) may add additional high priority consumers 520 to the node 505B. In one embodiment, the administrator may change one or more of the medium or low priority consumers 525, 530 to be high priority consumers 520. Or the administrator may assign additional computing resources to the processing node 505B which can be used to execute newly added high priority consumers 520. In this manner, the number of consumers in the processing nodes 505 can be altered to adapt to different workloads. Moreover, as workload increases or decreases generally (e.g., the number of high, medium, and low priority health events increase or decreases as a whole), the number of consumers in the processing nodes can be adapted to the changing workload.

Figure 6:
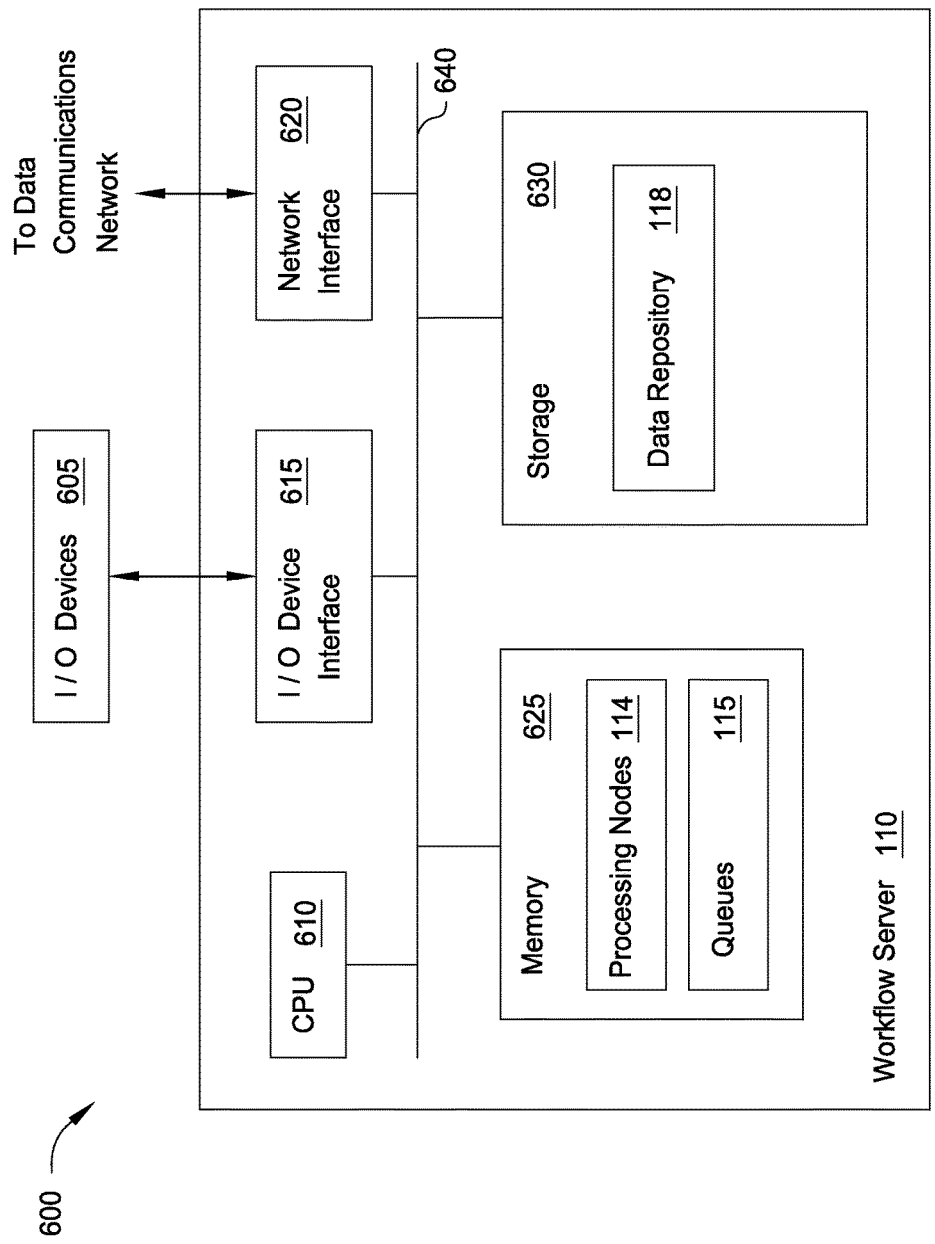
FIG. 6 illustrates a computing environment for processing health events, according to one embodiment.

FIG. 6 illustrates a computing environment 600 for processing health events, according to one embodiment. As shown, workflow server 110 includes, without limitation, a central processing unit (CPU) 610, a network interface 620, a memory 625, and storage 630, each connected to a bus 640. The workflow server 110 may also include an I/O device interface 615 connecting I/O devices 605 (e.g., keyboard, display and mouse devices) to the environment 110. Further, in context of this disclosure, the computing elements shown in the workflow server 110 may correspond to a physical computing system (e.g., a system in a data center) or may be a virtual computing instance executing within a computing cloud.

CPU 610 retrieves and executes programming instructions stored in memory 625 as well as stores and retrieves application data residing in the storage 630. The bus 640 is used to transmit programming instructions and application data between CPU 610, I/O devices interface 605, storage 630, network interface 620, and memory 625. Note, CPU 610 is included to be representative of a single CPU, multiple CPUs, a single CPU having multiple processing cores, and the like. Memory 625 is generally included to be representative of a random access memory. Storage 630 may be a disk drive storage device. Although shown as a single unit, storage 630 may be a combination of fixed and/or removable storage devices, such as fixed disc drives, removable memory cards, network attached storage (NAS), or a storage area-network (SAN).

Illustratively, memory 625 includes the processing nodes 114 and queues 115, while storage 630 includes the data repository 118. The processing nodes 114 may be assigned to the same CPU 610 or to different CPUs. Further, each processing node 114 may include respective sets of consumers (e.g., processes or threads) that are assigned to process different priority health events. The consumers monitor upstream queues 115, and when idle, retrieve and process health events that are assigned the same priority level.

One embodiment of the present disclosure is implemented as a program product for use with a computer system. The program(s) of the program product defines functions of the embodiments (including the methods described herein) and can be contained on a variety of computer-readable storage media. Examples of computer-readable storage media include (i) non-writable storage media (e.g., read-only memory devices within a computer such as CD-ROM or DVD-ROM disks readable by an optical media drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present disclosure, are embodiments of the present disclosure. Other examples media include communications media through which information is conveyed to a computer, such as through a computer or telephone network, including wireless communications networks.

In general, the routines executed to implement the embodiments of the present disclosure may be part of an operating system or a specific application, component, program, module, object, or sequence of instructions. The computer program of the present disclosure is comprised typically of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the disclosure. However, it should be appreciated that any particular program nomenclature that follows is used merely for convenience, and thus the present disclosure should not be limited to use solely in any specific application identified and/or implied by such nomenclature.

As described, embodiments herein provide techniques for processing health events in a workflow based on different priority levels. The processing nodes may include respective sets of consumers that are assigned to process health events with different priority levels. Advantageously, the system can adapt to changing different workloads by adding or removing event engines/servers as well as changing the number of consumers in the processing nodes.

While the foregoing is directed to embodiments of the present disclosure, other and further embodiments of the disclosure may be devised without departing from the basic scope thereof, and the scope thereof is determined by the claims that follow.

What is claimed is:

1. A method, comprising:
   receiving a health event for a patient derived from biometric data generated by one or more sensor devices;
   identifying a type of the health event by classifying the biometric data associated with the health event;
   storing the health event in a first one or more queues for processing, wherein the health event comprises an associated priority;
   monitoring the first one or more queues using a plurality of consumers operating on a first processing node, the plurality of consumers comprising a first number of high priority consumers assigned to process higher priority health events and a second number of low priority consumers assigned to process lower priority health events;
   processing the health event using a first consumer, of the plurality of consumers, and generating a second health event relating to the health event;
   storing the second health event in a second one or more queues for processing;
   monitoring the second one or more queues using a second plurality of consumers operating on a second processing node, wherein the second plurality of consumers comprises a third number of high priority consumers and wherein the third number of high priority consumers is greater than the first number of high priority consumers; and
   processing the second health event using a second consumer, of the second plurality of consumers.

2. The method of claim 1, further comprising:
   changing a number of consumers in one of the plurality of consumers and the second plurality of consumers in response to a change in a number of health events received for processing.

3. The method of claim 1, wherein, each of the consumers in the plurality of consumers comprises a thread that performs a same process on received health events as the other consumers in the plurality of consumers.

4. The method of claim 1, further comprising:
   receiving observation data generated by the one or more sensor devices, wherein the observation data includes both the biometric data and environmental data;
   evaluating the observation data using one of the first processing node or the second processing node to generate a derived observation based on previous observations stored in a data repository; and
   upon determining the derived observation satisfied a condition, triggering a different health event to be processed by the processing node, wherein the different health event comprises the derived observation.

5. The method of claim 1, further comprising:
   generating a new health event using one of the first processing node or the second processing node based on determining whether a condition corresponding to a rule has been satisfied.

6. The method of claim 1, further comprising storing a third health event in the second one or more queues for processing, wherein the second one or more queues store more high priority health events than the first one or more queues.

7. The method of claim 1, wherein second plurality of consumers perform a different process on received health events than the plurality of consumers.

8. The method of claim 1, wherein the health event is received at a workflow server and wherein the health event is generated by classifying the biometric data at one of: (i) a mobile device or (ii) a sensor device of the one or more sensor devices and wherein processing the health event comprises re-classifying the health event, using the workflow server, as the second health event.

9. The method of claim 8, wherein the second health event comprises a higher priority than the health event and wherein the second consumer is a high priority consumer.

10. The method of claim 9, wherein processing the second health event comprises providing the second health event to an action service and wherein the action service is configured to take an action based on the second health event.

11. The method of claim 10, wherein the action comprises forwarding the second health event to a monitoring service configured to allow review of the health event by a care provider for the patient.

12. A non-transitory computer-readable medium containing computer program code that, when executed by a processor, performs an operation for outputting information for display, the operation comprising:
   receiving a health event for a patient derived from biometric data generated by one or more sensor devices;
   identifying a type of the health event by classifying the biometric data associated with the health event;

storing the health event in a first one or more queues for processing, wherein the health event comprises an associated priority;

monitoring the first one or more queues using a plurality of consumers operating on a first processing node, the plurality of consumers comprising a first number of high priority consumers assigned to process higher priority health events and a second number of low priority consumers assigned to process lower priority health events;

processing the health event using a first consumer, of the plurality of consumers, and generating a second health event relating to the health event;

storing the second health event in a second one or more queues for processing;

monitoring the second one or more queues using a second plurality of consumers operating on a second processing node, wherein the second plurality of consumers comprises a third number of high priority consumers and wherein the third number of high priority consumers is greater than the first number of high priority consumers; and processing the second health event using a second consumer, of the second plurality of consumers.

13. The non-transitory computer-readable medium of claim 12, the operation further comprising:
changing a number of consumers in one of the plurality of consumers and the second plurality of consumers in response to a change in a number of health events received for processing.

14. The non-transitory computer-readable medium of claim 12, wherein, each of the consumers in the plurality of consumers comprises a thread that performs a same process on received health events as the other consumers in the plurality of consumers.

15. The non-transitory computer-readable medium of claim 12, the operation further comprising:
receiving observation data generated by the one or more sensor devices, wherein the observation data includes both the biometric data and environmental data;
evaluating the observation data using one of the first processing node or the second processing node to generate a derived observation based on previous observations stored in a data repository; and
upon determining the derived observation satisfied a condition, triggering a different health event to be processed by the processing node, wherein the different health event comprises the derived observation.

16. The non-transitory computer-readable medium of claim 12, the operation further comprising:
generating a new health event using one of the first processing node or the second processing node based on determining whether a condition corresponding to a rule has been satisfied.

17. A system, comprising:
at least one sensor device to collect biometric data associated with a patient;
a workflow server comprising a first and second interconnected processing node, the workflow is configured to:
receive a health event for a patient derived from biometric data generated by the at least one sensor device;
identify a type of the health event by classifying the biometric data associated with the health event;
store the health event in a first one or more queues for processing, wherein the health event comprises an associated priority;
monitor the first one or more queues using a plurality of consumers operating on the first processing node, the plurality of consumers comprising a first number of high priority consumers assigned to process higher priority health events and a second number of low priority consumers assigned to process lower priority health events;
process the health event using a first consumer, of the plurality of consumers, and generating a second health event relating to the health event;
store the second health event in a second one or more queues for processing;
monitor the second one or more queues using a second plurality of consumers operating on the second processing node, wherein the second plurality of consumers comprises a third number of high priority consumers and wherein the third number of high priority consumers is greater than the first number of high priority consumers; and
process the second health event using a second consumer, of the second plurality of consumers.

18. The system of claim 17, wherein the workflow server is configured to change a number of consumers in one of the plurality of consumers and the second plurality of consumers in response to a change in a number of health events received for processing.

19. The system of claim 17, wherein, each of the consumers in the plurality of consumers comprises a thread that performs a same process on received health events as the other consumers in the plurality of consumers.

20. The system of claim 17, wherein the workflow server further comprises:
a plurality of event engines, each comprising one or more processing nodes for processing health events received from at least one sensor device; and
a load balancer configured to receive the health event and assign the health event to one of the plurality of event engines.

* * * * *